United States Patent
Field

[11] Patent Number: 5,620,609
[45] Date of Patent: Apr. 15, 1997

[54] PROCESS AND APPARATUS FOR DEWATERING CONTROLLED BY MONITORING LIGHT SCATTERED BY SUPERNATANT

[75] Inventor: John R. Field, West Yorkshire, United Kingdom

[73] Assignee: Allied Colloids Limited, West Yorkshire, United Kingdom

[21] Appl. No.: 464,836

[22] PCT Filed: Jan. 21, 1994

[86] PCT No.: PCT/GB94/00119

§ 371 Date: Jun. 27, 1995

§ 102(e) Date: Jun. 27, 1995

[87] PCT Pub. No.: WO94/17394

PCT Pub. Date: Aug. 4, 1994

[30] Foreign Application Priority Data

Jan. 22, 1993 [GB] United Kingdom ............. 9301261

[51] Int. Cl.⁶ ............................................ B01D 21/32
[52] U.S. Cl. ................. 210/745; 73/61.69; 210/94; 210/198.1; 210/709; 210/770
[58] Field of Search ................. 73/61.65, 61.68, 73/61.69; 210/94, 96.1, 138, 139, 143, 198.1, 513, 745, 770, 776, 800

[56] References Cited

U.S. PATENT DOCUMENTS

| | | |
|---|---|---|
| 3,309,956 | 3/1967 | Hach . |
| 3,869,903 | 3/1975 | Beach et al. ........................ 73/61.65 |
| 4,116,832 | 9/1978 | Tardivel ............................. 210/800 |
| 4,194,391 | 3/1980 | Rosenberger ..................... 73/61.69 |
| 4,318,296 | 3/1982 | Parker et al. ..................... 73/61.69 |
| 4,876,881 | 10/1989 | Pope ................................ 73/61.65 |

FOREIGN PATENT DOCUMENTS

| | | | |
|---|---|---|---|
| 2055874 | 4/1971 | France . | |
| 1300347 | 3/1987 | U.S.S.R. ................ | 73/61.65 |

OTHER PUBLICATIONS

International Search Report for PCT/GB 94/00119, 27 Apr. 1994.

*Primary Examiner*—Joseph W. Drodge
*Attorney, Agent, or Firm*—Sughrue, Mion, Zinn, Macpeak & Seas

[57] ABSTRACT

A sedimentation or other dewatering process conducted on a suspension is controlled by filling a body (1) that is open at its top end (2) with the suspension, establishing quiescent conditions and allowing the suspension to settle to form a supernatant layer at the top end (2), generating light from an assembly (14) and measuring the amount of scattered light (19) from the supernatant layer by a collector (21) and utilizing the measured amount of scattered light to control the dewatering.

15 Claims, 3 Drawing Sheets

PROCESS AND APPARATUS FOR DEWATERING CONTROLLED BY MONITORING LIGHT SCATTERED BY SUPERNATANT

The present invention relates to the control of processes for dewatering suspensions, especially coagulation and/or flocculation followed by sedimentation, in response to measurement of turbidity.

Various systems are known for determining the turbidity of a liquid. Many of the systems involve filling a cell of glass or transparent plastic and determining the optical properties of the cell filled with the liquid. Such systems in which optical properties are determined using an arrangement where a transparent material is in contact with the liquid all suffer from the disadvantage that contamination of the transparent material will influence the results.

A system that avoids this disadvantage is the Surface Scatter Turbidimeter SS6 manufactured by the Hach Company (see U.S. Pat. No. 3,309,956). In this system there is a upwardly extending elongate body defining a longitudinal central bore and having an open upper end, a feed positioned to feed suspension continuously into the body below the upper end, a collector positioned around the upper end to collect suspension that overflows from the upper end while defining a liquid surface at the open upper end, a light source positioned to direct a ray of light to strike this liquid surface at an angle such that light is scattered from it, and a collector positioned to receive the scattered light. In use, the suspension under test is forced to flow continuously upwardly through the body so as to provide a continuously replenished fresh layer of suspension at the upper surface which is typical of the whole body of the suspension, and the scattering of light from this typical upper surface is a measure of the turbidity of the suspension that is being tested. In order that measurable results can be achieved it is, of course, necessary that the suspension should be dilute and have adequate light scattering properties. This system would be inoperable if used with a suspension that did not have adequate light scattering properties.

There are many industrial processes where a suspension is dewatered by, for instance, sedimentation, filtration or centrifugation. Examples include sewage sludge, papermaking thinstocks and thickstocks, and inorganic suspensions. It is standard practice to flow such a suspension though a service line towards a dewatering plant where the suspension is dewatered, and to flocculate or otherwise chemically modify the suspension prior to dewatering by adding polymeric flocculant or other chemical dewatering modifier by appropriate chemical dosing equipment. Optimum dewatering depends on the nature of the suspension, but this tends to be variable. Accordingly various techniques have been developed for controlling the dewatering, either manually or automatically, in response to measurement of some physical property of the suspension.

In particular, it is known to use supernatant or filtrate turbidity measurements for monitoring and controlling sedimentation or other dewatering processes, especially when the clarity of the supernatant or filtrate is important. Usually an optimum turbidity is determined for a particular process by running plant trials of the process under different conditions, typically with different amounts or types of dewatering treatment chemical. Subsequently, when the process is run commercially, the process conditions are adjusted to maintain the turbidity at the optimum predetermined level.

In a typical process, the suspension to be dewatered flows along a conventional service flow pipeline, past a dosing point at which a dewatering treatment chemical is added to the suspension to a dewatering plant at which it is allowed to settle. Settling of the suspension usually takes place in a large sedimentation tank and may take two hours or more. After settling, turbidity measurements are taken on the supernatant. If this is done using a turbidimeter submerged in the tank or after the tank, it is necessary to wait for settlement before useful turbidity measurements can be taken. This means that the overall treatment process will have advanced considerably before any change in dosing of treatment chemical can be effected in response to the measured turbidity. Therefore the treatment process may run inefficiently for some periods of time and may never reach full efficiency.

Measurement may alternatively be by removing a sample of the suspension from the pipeline and placing it in a stand-alone turbidimeter which is designed to generate in a shorter period a sufficient volume of supernatant on which turbidity measurements can be conducted. Although the necessary settlement period can be less than the two or more hours generally required in a settlement tank, in practice it is generally still necessary to leave the suspension for quite a long time (e.g. half an hour or more) to allow sufficient settlement to permit meaningful turbidity measurements to be conducted by available apparatus. Accordingly the overall treatment process will still have advanced before the need to modify the dewatering conditions has become apparent and so the process is rather inefficient. Also, sampling from the service line to the laboratory analytical apparatus is inconvenient and makes automatic control of the process difficult to achieve.

Many of the suspensions that come into question have a tendency to foul apparatus that they contact. Accordingly a problem when the turbidimeter is submerged in the suspension, (for instance in or after the sedimentation tank) is that it is likely to suffer fouling with the result that it has to be cleaned frequently and normally will have to be removed from the process to permit adequate cleaning. Stand-alone turbidity meters can be cleaned in position, but the careful cleaning needed to obtain reliable results is inconvenient.

It would be desirable to provide a way of monitoring, and controlling, sedimentation or other dewatering processes using turbidity measurements and which has a quicker response time than prior art processes, and which therefore allows substantially immediate alteration of the process in accordance with the current properties of the suspension. It would also be desirable to provide a process in which there is less risk of the turbidimeter measurements being rendered unreliable by fouling. It would also be desirable to provide such a process which could be conducted substantially on-line with the service flow of suspension to be sedimented.

According to the present invention a process for monitoring dewatering of a suspension comprises the steps of providing an upwardly extending elongate body defining a longitudinal central bore and having an open upper end, filling the body with suspension until a surface of suspension is formed across the open end, establishing quiescent conditions and allowing the suspension to settle to form a supernatant layer, directing a ray of light to strike the surface at an angle such that light is scattered by the supernatant layer, positioning a collector to receive light scattered by the supernatant layer, measuring by the collector the amount of scattered light it receives from the supernatant layer, and utilising the amount of scattered light measured by the collector to control dewatering of the suspension.

The process is extremely rapid to operate since meaningful measurements can be obtained as soon as a thin supernatant layer has formed by settlement. Since the optical measurements are conducted on the liquid surface, rather than through a glass cell, inaccuracies due to fouling of a cell containing the liquid are avoided.

When the upper liquid surface is first formed across the open end, the top part of the liquid will have the same composition as the remainder of the liquid in the body. Usually the optical density of the suspension is too high to give meaningful turbidity values at this stage from within the suspension, and even if a meaningful turbidity value is obtained on the freshly formed surface of the suspension, the value will be of the suspension itself. This is of little or no assistance in the invention, where the need is to determine the turbidity value of the supernatant obtained upon settling the suspension. Depending upon the nature of the suspension, settlement may either lead to the formation of a relatively clear mud line between supernatant of substantially uniform solids content above the line and sediment below the line, or it may lead to a supernatant through which solid content increases gradually downwards. Either way, after allowing settling to occur the solids content at the top of the column of liquid will be less than at lower positions.

The dewatering process in the invention can be controlled either in response to a constant turbidity value that is recorded or in response to the relationship between time and the change in turbidity.

Light that strikes the top of the liquid, generally near the centre of the open liquid surface, will be scattered by the particles it encounters. A collector is positioned above the settled layer to collect light that is scattered generally at approximately right angles to the centre of the surface. Before settling starts, all the scattering of light will be from the unsettled suspension. Once settling has started, the scattering of light will be due to particles in the supernatant and, if the supernatant layer is thin, to scattering in the unsettled suspension (below the mud line if there is one). As the mud line sinks, the location of the scattered light that is scattered from below the mud line will move with respect to the collector. The collector can be so positioned that when the supernatant is deep enough none of the light scattered from below the mud line will reach the collector. Accordingly, the amount of scattered light that reaches the collector (and therefore the recorded or apparent turbidity) may start high, due to a substantial amount of scatter from below the mud line, but will drop to a substantially constant value that is due solely to scatter in the supernatant, settled, layer. Typically, the constant value is obtained while the layer is still shallow, e.g. up to 10 mm or 20 mm thick. Useful measurements (e.g. of the rate of change of collected scattered light) can be obtained with even thinner layers.

It will thus be apparent that in some processes of the invention settling is allowed to occur until the amount of scattered light recorded by the collector is substantially constant, and this constant value is utilised to control the dewatering of the suspension. This constant value is a function of the suspended matter in the supernatant layer only since in such processes the collector receives substantially no light from the supernatant layer that was scattered from below the mud line, when the value is constant. If it is desired only to rely upon this constant value, then the collector can be at a position to receive and measure only scattered light from within the supernatant at a chosen time after establishing quiescent conditions, this position being such that a substantially constant amount of scattered light is received by the collector.

Instead of or in addition to relying upon this constant value for controlling the dewatering, reliance is often placed on the relationship between the amount of scattered light measured by the collector and the time after establishing quiescent conditions. For this purpose, the collector is positioned to receive and measure light scattered from within and beneath the supernatant layer at one time after establishing quiescent conditions and to receive and measure light scatted wholly or mainly from within the supernatant layer at a later time. Often, the process is conducted by recording initially the relationship between time and scatter and, subsequently by recording the substantially constant value.

Since the constant value can be determined on a layer which is quite thin (e.g. under 10 mm or 20 mm thick), determination of this constant value can be achieved quickly after establishing quiescent conditions. Since meaningful measurements (and in particular the rate of change of scatter) can be determined on even thinner layers, meaningful results can be achieved even before then. Thus, by the invention, it is possible, after a settling period of only a few seconds or minutes, to obtain results by which the dewatering process can be controlled.

The process can be conducted as a manual, stand-alone process, with the suspension being poured into the body and the timing and the observations being conducted manually. Preferably, however, there is some degree of automation. Suitable novel apparatus for performing the invention comprises an upwardly extending elongate body defining a longitudinal central bore and having an open upper end, a valved feed position to feed suspension into the body and means for closing this feed, a light source positioned to direct a ray of light to strike the surface at an angle such that light is scattered from the liquid at the open upper end, a light collector positioned to receive light scattered from the liquid at the open upper end, timing means by which the time between closing the valved feed and recording one or more measurements of scattered light is automatically controlled or recorded, and signal means for generating a signal in response to the measurement of scattered light.

The method can be conducted remote from a service line though which the suspension is flowing, to generate a signal that can be transmitted to a remote dewatering process. For instance the apparatus may be used at a laboratory to which a batch of the suspension is taken and can be used to generate a numerical or other display in print-out or other signal form that can be used manually to control the sedimentation or other dewatering of the bulk suspension from which the sample was taken. Similarly, when the method is being conducted close to the service line, with the suspension being fed through a valved feed from the service line to the body, the apparatus can provide a display to assist manual control of the dewatering process. Preferably, however, the apparatus includes control means for controlling the dewatering process and these control means are constructed to be controlled automatically in response to the amount of scattered light measured by the collector. Thus there should be appropriate signal means to generate a signal which controls the dewatering.

Suspension can be run off from the service flow either direct into the open top of the body or into a vessel by which the suspension can be transported to the apparatus or, preferably, the body is in fluid communication with the service flow (e.g. a carrier duct or pipeline) through a screened valved inlet suitable for feeding the suspension from the pipeline into the body. Accordingly the invention can provide an on-line method of controlling the dewatering process.

Generally the suspension is flowing from a dosing pump or other stage at which was added a chemical dewatering modifier.

Preferably, the body is filled through a valved feed and conveniently this valved feed leads from a service line by which suspension is flowing to a dewatering apparatus. The valved feed can discharge into the top of the body, but preferably is a valved inlet that leads into the body at a position below the open upper end. When a timer is incorporated with such an apparatus, the feeding of the suspension into the body, the establishment of quiescent conditions and the measurement of scattered light are preferably all controlled automatically by the timer.

Thus a typical sequence will involve filling the body with the suspension, stopping the filling and thereby establishing quiescent conditions and determining the amount of scattering at a predetermined or measured time after stopping the filling.

It is often preferred for the suspension to settle sufficient to give a supernatant layer having sufficient depth to give meaningful turbidity measurement of the supernatant. Accordingly the timer may be such that the suspension is settled for a predetermined period before some measurements are taken. This period may be a relatively arbitrary period that is known to be sufficient to allow a sufficient supernatant layer to form or it can be a period that is selected reasonably accurately, and as short as possible, having regard to the anticipated settling properties of the suspension.

The amount of light scattered off the surface of the suspension may be measured through the predetermined period (either continuously through it or, for instance, through the later stages of it) or after the predetermined period (for instance either a substantially instantaneous measurement at the end of the period or several measurements after the predetermined period).

Instead of controlling the measurement of scatter after a predetermined time, the timer may be constructed to determine the time at which a predetermined amount of scattered light is measured. For instance the result of the process might be a time value that is required to achieve a particular level of turbidity, rather than a turbidity value achieved after a particular time.

In one typical process, the suspension is settled for a predetermined time and the amount of light scattered off the surface of the liquid onto the collector is measured up to the predetermined time or at or after that time and the measured amount of light is utilised to generate the signal that is used to control the dewatering process.

In another typical process, the suspension is settled for sufficient time to allow the rate of change of the amount of scattered light to reach a predetermined value. The amount of scattered light is measured throughout this period. The amount of scattered light at a predetermined value for the rate of change and/or the time required to reach this chosen value is utilised to control the dewatering of the suspension.

In another typical process, the suspension is settled for sufficient time for the amount of scattered light to reach a chosen value. The amount of scattered light is measured through this period. The time required to reach this chosen value is utilised to control the dewatering of the suspension.

When utilising the time required for the amount to reach a particular value, it is usually preferred to utilise the time required to change from one predetermined value to another can be used to control the suspension.

The upwardly extending elongate body that is to contain the test suspension can extend in a vertical direction or in a direction that forms an angle (for instance 20° to 60°) to the vertical. The body is typically made of plastic. It may have dimensions of 10 to 50 cm in length and 5 to 20 cm in width. The top of the body preferably has a generally flat horizontal lower edge which can conveniently serve as a weir over which the suspension can uniformly flow. Accordingly, it can be convenient for the top of the body, and often the entire body, to have square cross section.

Generally the elongate body extends upwards from a base which acts as a support and may close the bottom end of the body.

The body may be filled with suspension either by pumping or otherwise directing flow of suspension through a screened valved inlet below the upper end and generally at or near its lower end or by pouring suspension into its upper end. Filling is continued until a surface layer of suspension is formed at the upper end.

It is normally preferred to conduct the filling until the suspension overflows the open end and generally means are provided for collecting suspension that overflows from the open end after formation of the desired surface of the suspension at the open end. The filling is then stopped.

Following settlement and the measurement of the turbidity of the settled upper layer of the batch of suspension in the body, the body is emptied and/or filled with a fresh batch of suspension for fresh measurement to be made. The body can be emptied by draining the suspension through an outlet in the bottom of the body. Drainage can be accelerated by connection to a vacuum pump. If the valved inlet is in the bottom of the body, the outlet may be the same opening as the inlet in which case a conventional two-way valve (or fill and draw valve) may be provided in the opening. Alternatively there may be a separate drain outlet which is closed during filling and measurement and which is opened to empty the body. Alternatively, if the body is portable, it can simply be inverted to empty it.

After emptying, the body can be refilled or it can be emptied by suspension in the body being flushed upwardly out of the body by up-flowing fluid introduced through an inlet at or near the base. The up-flowing fluid can be fresh suspension or water or other wash liquor.

It is convenient for the invention to be performed utilising the novel apparatus that includes timing means that can be pre-programmed to permit a predetermined settling period after termination of the filling of the body with the suspension and before the generation of the final signal that is used for controlling the dewatering process. However the invention can also be conducted (less efficiently) using simpler forms of apparatus, for instance where the plant operator manually terminates filling, estimates an appropriate settling period, and then switches on the light source and the measuring means.

The control of the dewatering process generally comprises changing the amount or type of dewatering modifier that is used to modify the dewatering properties, and which generally is added before the sample is subjected to the turbidity measurement.

The chemical dewatering modifier can be any chemical material that has an effect on the dewatering properties, and in particular on the clarity of the filtrate or supernatant. Generally the chemical is a polymeric flocculant which has a high molecular weight (e.g. intrinsic viscosity above 4 dl/g) and is of the type that is commonly referred to as a bridging flocculant, but if desired the chemical can be a low molecular weight (e.g. intrinsic viscosity below 3 dl/g), highly ionic, polymeric flocculant which is more accurately generally referred to as a coagulant. Other chemicals that can be used included inorganic coagulants such as multivalent metal salts, natural polymers such as starch or cationic starch, polyethylene imine, polyethylene oxide, and some inorganic materials such as polysilisic acid and derivatives of this, and swelling clays, generally known as bentonites. Usually, however, a polymeric bridging or coagulant flocculant is used.

The dewatering process is generally a sedimentation stage or can be, for instance, a filtration or centrifugation stage. When the dewatering process conditions are variable, e.g. the pressure of filtration or the speed or centrifugation, such conditions of dewatering can be controlled in response to the turbidity measurement obtained in the invention instead of or in addition to controlling the dosing of chemicals.

The process and apparatus of the present invention are suitable for use on any suspension that is capable of settling in a useful manner. The solids content can be low (e.g. below 1% by weight) when the suspension is colloidal and/or organic, but can be much higher provided the suspended matter is such that it can settle to leave an upper supernatant. For instance many inorganic materials will settle in this manner when the solids content is up to 20% by weight or even more. Typical suspensions are raw sewage (e.g. 10 to 1000 ppm), secondary sewage (e.g. 500 to 5000 ppm), and pigments, non-swelling clays and coal tailings (e.g. 1 to 20%).

The invention is illustrated in the accompanying drawings in which

Figure 1:
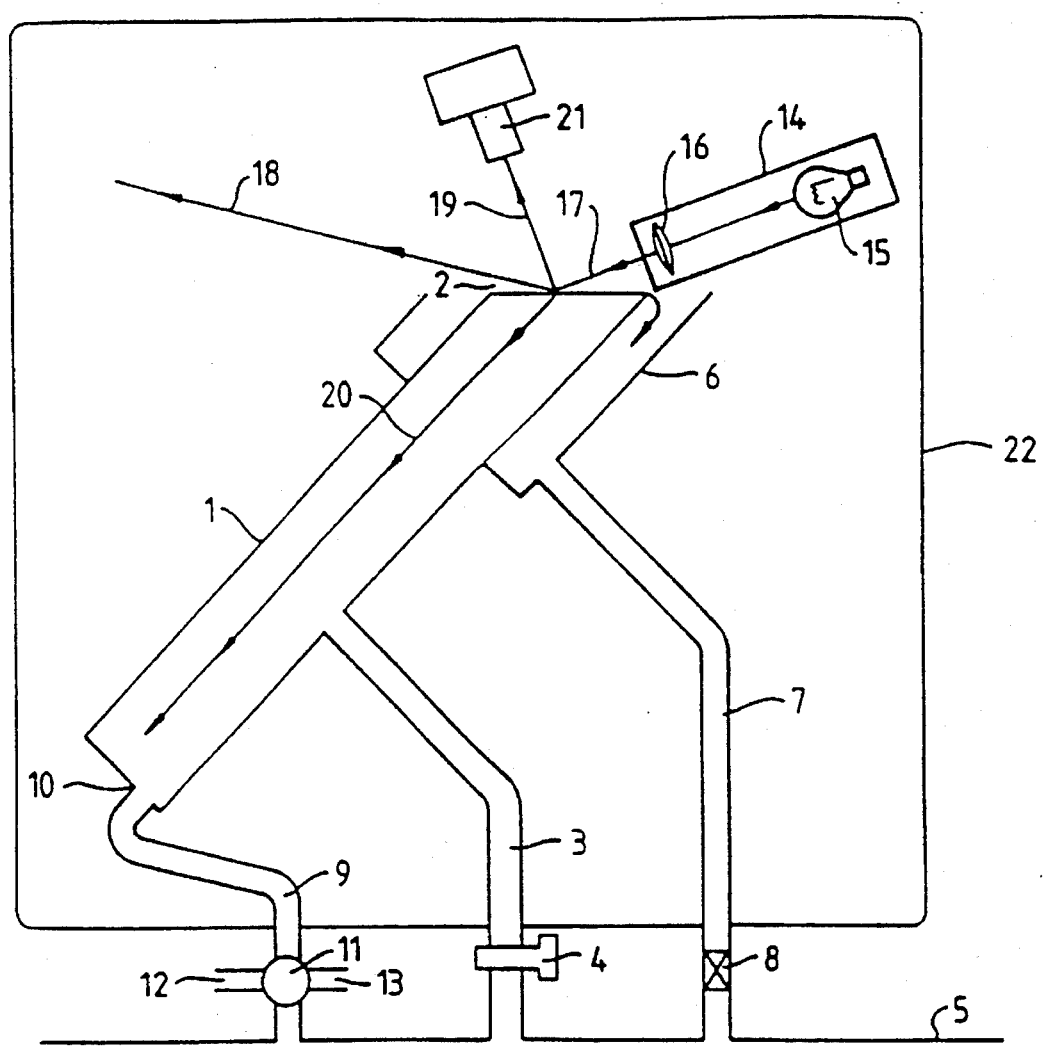
FIG. 1 shows a diagrammatic side view of suitable apparatus in fluid communication with a service flow pipeline (not to scale).

The apparatus comprises an inclined cylindrical body 1 that is open at its top end 2. An inlet line 3 including a valve 4 provides fluid communication between a service flow line 5 for sewage or other suspension and the body 1. A collecting cylinder 6 surrounds the top end of the body and is positioned to collect the fluid that overflows the top end 2 as a result of the body being filled through inlet 3. A drain line 7 leads from the base of the cylinder through a non-return valve 8 back into the service line. Alternatively, it can lead to drain.

A line 9 leads from the bottom end 10 of the cylinder to a valve 11 by which the line can be opened or closed. If the line is to be used merely for drainage at the end of a process, it may be adequate merely for the line 9 and valve 11 to discharge into the service line 5 or it may discharge to drain (not shown). Often, however, line 9 is used for backwashing the cylindrical body 1 either with water from a supply shown diagrammatically as 12 or by pumping suspension from the line 5 by a pump (not shown). Instead of or in addition to this, there may be an air line 13 by which vacuum or compressed air can be passed through the line 9. If line 9 is constructed to allow suspension to be forced from line 5, through line 9, into the body 1 it may be appropriate to rely on line 9 for this and to omit line 3.

There is a lamp assembly 14 including a lamp 15 and a lens 16 by which a ray of light 17 can be directed onto the upper surface of the liquid in the open top end 2 of the body 1. Some of the light striking the surface is reflected as a reflected ray 18, some is refracted as a refracted ray 20 and some is scattered by particles in the upper liquid layer as scattered light 19. A photocell 21 is positioned to receive the scattered light 19. Instead of using a photocell, other conventional light collectors can be used such as photomultipliers and light sensitive diodes.

Suitable apparatus can be constructed by making appropriate modifications, for instance to the valves and to the method of operation, of a Surface Scatter Turbidimeter SS6 manufactured by the Hach Company.

The whole apparatus conveniently is enclosed within a protective housing 22.

The service line 5 typically leads from a flocculant dosing point to a sedimentation tank. It may be an open duct or a closed pipe and the line 3 (and/or the line 9 if it is to receive fluid from the service line 5) must naturally be connected into the line 5 in an appropriate manner such that fluid can pass from the line 5 into the cylindrical body 1. When the line 5 is pressurised the pressure of the fluid in the line may be sufficient, but otherwise it may be necessary to provide appropriate pumps, not shown.

In use, suspension from the line 5 is flowed through the inlet line 3 to fill the body 1 and to overflow from the top end 2 of the body into the cylinder 6, from which it drains through the drain outlet 7 and the non-return valve 8 back into line 5. The valve 4 is then closed and the suspension in the cylinder 1 allowed to settle for a predetermined time. The ray of light 17 is then generated and the scattered light 19 is recorded by the photocell either at a predetermined time or after a predetermined degree of settlement (as shown by the position of the mud line), or more usually over a predetermined time range.

There will usually be automatic timing means (not shown) for controlling the settling time (between closing the valve 4 and making optical measurement) and also for controlling and/or recording the times of successive measurements taken during settling of the same batch of suspension. There may also be electronic communication (not shown) between the photocell 21 and the apparatus for controlling the dosage of flocculant, and/or between the photocell and display apparatus for display of the result of the measurement.

Since the sewage or other suspension does not contact the optical apparatus, the risk of errors due to contamination of the optical surfaces is much less than in conventional systems.

The following is an example to further illustrate the process of the present invention in use as a system for monitoring (and controlling) the sedimentation of a suspension.

EXAMPLE

The suspensions under test were 1% slurries of chalk and filler clay.

300 ml of each of the slurries were treated with varying doses of cationic polyacrylamide flocculant (available from Allied Colloids Limited under the trade name Percol 63, Percol being a trade mark) in a liter measuring cylinder and inverted 4 times to ensure complete mixing. Each was then used to overfill the calibration cylinder in a Hach Surface Scatter 6 Turbidimeter SS6. As soon as filling stopped a stopwatch was started and the turbidity noted at various time intervals.

The turbidimeter was set to average the turbidity over every period of 60 seconds of each test run, and so the earlier readings in the first 60 seconds are not meaningful.

Figure 2:
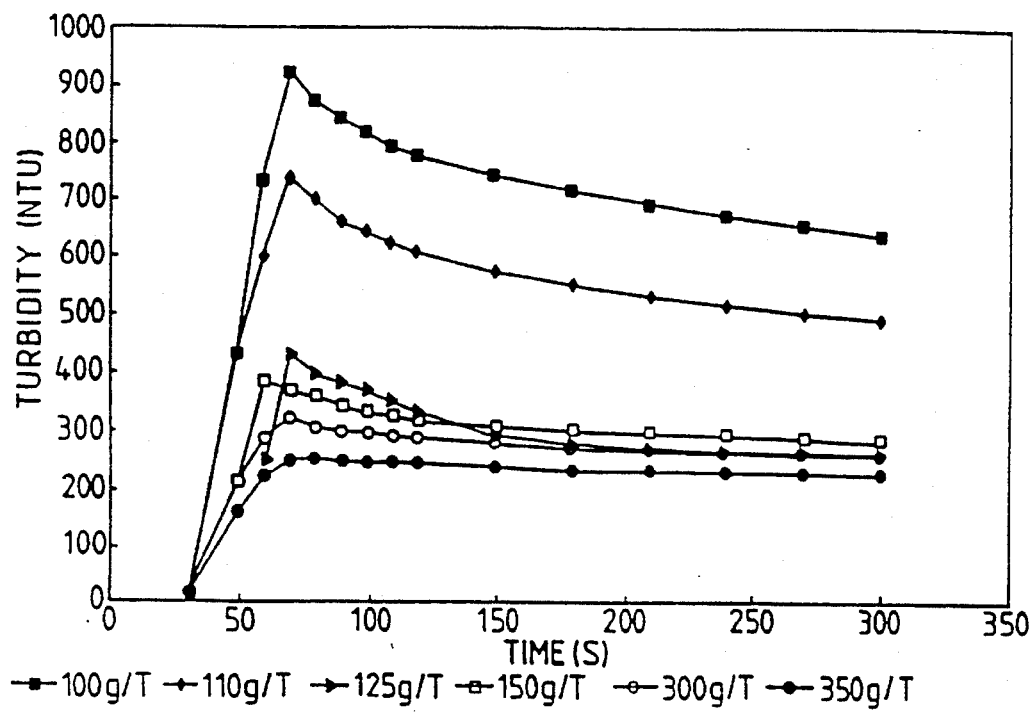
FIGS. 2 to 5 are graphs showing changes in the recorded value of the turbidity of the settled supernatant layer.
Figure 3:
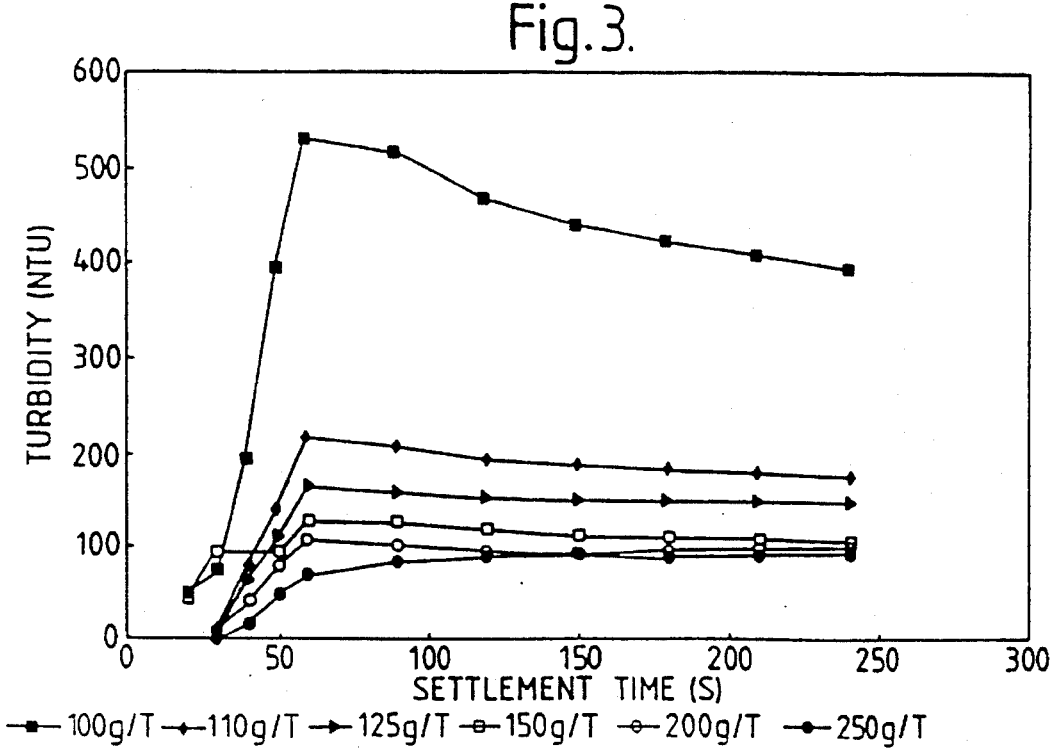

FIGS. 2 and 3 are graphs showing the variation of turbidity with time for the different doses of flocculant used on the chalk and clay suspensions respectively.

Figure 4:
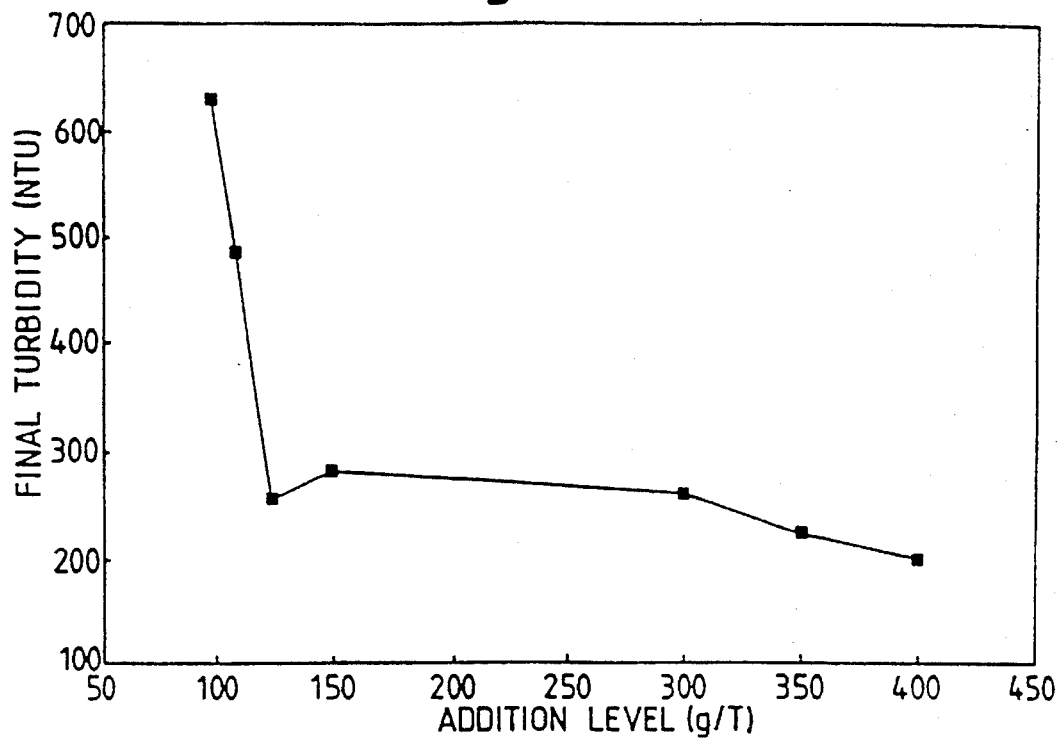
Figure 5:
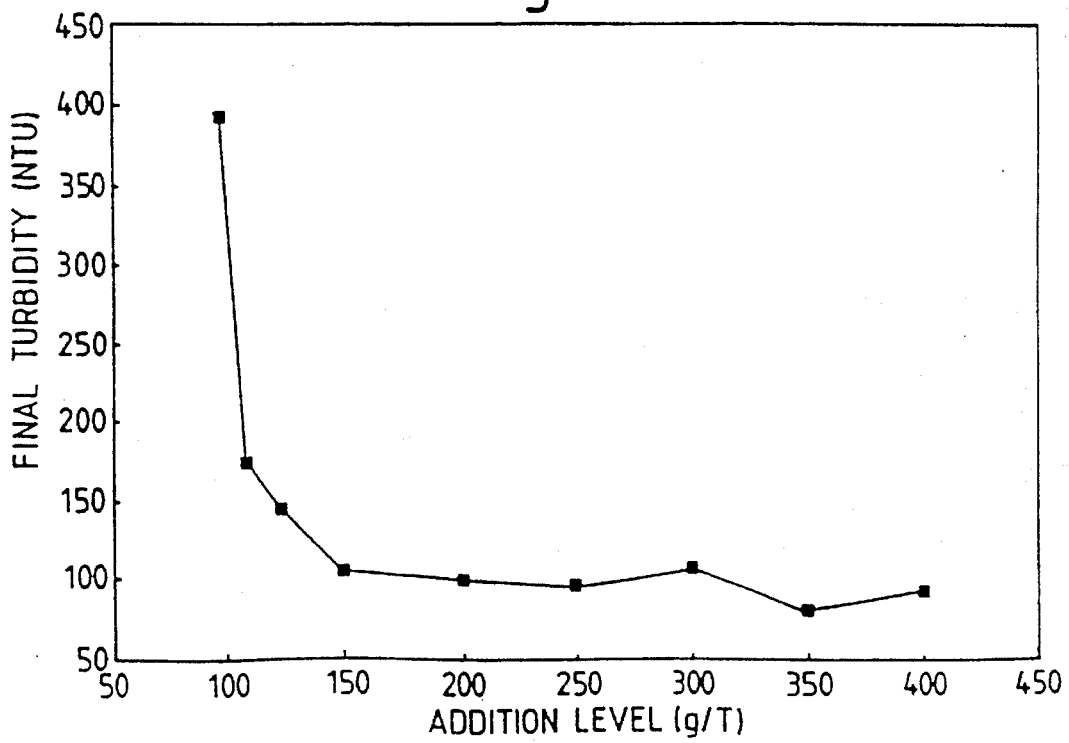

FIGS. 4 and 5 are graphs showing the average turbidity for the different doses of flocculant used on the chalk and clay suspensions respectively.

The results show that flocculant effectiveness on chalk and clay can be predicted by turbidity measurements using the process of the present invention.

I claim:

1. A process for controlling dewatering of a suspension in response to determining turbidity of a supernatant obtained from the suspension, which comprises the steps of:

providing an upwardly extending elongate body defining a longitudinal central bore and having an open upper end, filling the body with a portion of the suspension until a surface of suspension is formed across the open end, establishing quiescent conditions and allowing the suspension portion to settle to form a supernatant layer, directing a ray of light to strike the surface at an angle such that light is scattered by the supernatant layer, positioning a collector to receive light scattered by the supernatant layer, measuring by the collector the amount of scattered light it receives from the supernatant layer at different times after establishing quiescent conditions and thereby determining a rate of change of the amount of scattered light after establishing quiescent conditions, and utilizing the rate of change of the amount of scattered light measured by the collector to control dewatering of the suspension.

2. A process according to claim 1 in which the settling is allowed to occur until the amount of scattered light recorded by the collector is substantially constant and this constant amount also is utilised to control the dewatering of the suspension.

3. A process according to claim 2 in which the collector is positioned to receive and measure only light scattered from within the supernatant at a chosen time after establishing quiescent conditions, which time is such that a substantially constant amount of scattered light is received by the collector.

4. A process according to claim 1 in which the suspension is a suspension that is being dewatered after addition of a chemical dewatering modifier and the control of dewatering is by controlling the addition of the dewatering modifier.

5. A process according to claim 4 in which the chemical dewatering modifier is a polymeric flocculent added to the suspension before the portion is filled into the body.

6. A process according to claim 1 in which the dewatering is by sedimentation.

7. A process according to claim 1 in which the suspension portion that is filled into the body is flowed through a valved feed to the body from a service line by which the suspension is flowing to be dewatered.

8. A process according to claim 7 in which the valved feed is a valved inlet that leads into the body at a position below the open upper end.

9. A process according to claim 7 or claim 8 in which the feeding of the suspension portion into the body, the establishment of quiescent conditions, and the measurement of scattered light are controlled automatically by timing means.

10. A process according to claim 1 in which the dewatering is controlled automatically in response to the measuring of scattered light.

11. A process according to claim 1 in which the body is an inclined body and is filled with the suspension portion until the suspension portion overflows the top end, and the filling is then stopped thereby establishing quiescent conditions.

12. Apparatus comprising an upwardly extending elongated body defining a longitudinal central bore having an open upper end, a valved feed positioned to feed a portion of a suspension into the body and means for closing the feed, a light source positioned to direct a ray of light to strike a liquid surface at the open upper end, a light collector positioned to receive light scattered from the liquid at the open upper end, and means for making measurements of the amount of received scattered light, and in which the apparatus also comprises timing means for automatically controlling or recording the respective times between closing the valved feed and making measurements of scattered light, means for determining the rate of change of the amount of scattered light over time and means for generating a signal in response to the measurements of the amount of scattered light.

13. Apparatus according to claim 12 in which the signal generating means include means for automatically controlling the dosage of a chemical dewatering modifier added to the suspension in response to the signal.

14. Apparatus according to claim 12 including means for connecting the valved feed to a service line.

15. Apparatus according to claim 12 including means for flushing settled suspension from the body and operable by the timing means after the generation of the signal.

* * * * *